United States Patent [19]

Sichak

[11] 4,201,765

[45] May 6, 1980

[54] PREPARATION FOR TREATING DERMATITIS IN THE NATURE OF TINEA PEDIS

[75] Inventor: Stephen Sichak, Dolton, Ill.

[73] Assignee: Scholl, Inc., Chicago, Ill.

[21] Appl. No.: 944,154

[22] Filed: Sep. 20, 1978

Related U.S. Application Data

[62] Division of Ser. No. 754,694, Dec. 27, 1976, Pat. No. 4,147,770.

[51] Int. Cl.$^2$ .......................... A61L 9/04; A01N 9/24; A61K 31/11
[52] U.S. Cl. ....................................... 424/45; 424/333
[58] Field of Search ........................... 424/333, 45, 46

[56] References Cited

PUBLICATIONS

Frear, A Catalogue of Insecticides and Fungicides, vol II, (1948), pub. Chronica Botanica Co., E. Waltham, Mass., p. 37.

Chemical Abstracts, vol. 69: 9880u (1968).

*Primary Examiner*—Donald B. Moyer
*Attorney, Agent, or Firm*—Hill, Van Santen, Steadman, Chiara & Simpson

[57] ABSTRACT

A preparation for treating dermatitis of the nature of tinea pedis or athlete's foot, which preparation may be applied directly to the foot as a cream, gel, powder, liquid, aerosol liquid, or aerosol powder, and may be held in a controlled release dispenser in a shoe or the like overnight to deodorize and sanitize the shoe for wear the next day without direct application of the preparation to the foot, relying on the residual effect of the overnight treatment in the shoe. The invention also embodies a method of using the preparation.

4 Claims, No Drawings

PREPARATION FOR TREATING DERMATITIS IN THE NATURE OF TINEA PEDIS

RELATED APPLICATION

This application is a division of Stephen Sichak U.S. patent application Ser. 754,694 filed Dec. 27, 1976 entitled "Preparation For Treating Dermatitis In The Nature Of Tinea Pedis" now U.S. Pat. No. 4,147,770 issued Apr. 3, 1979.

BRIEF SUMMARY OF THE INVENTION

At the outset, it may be mentioned that as to prior art, the most pertinent to the instant invention known at present comprises two published articles, as follows:
 (A) An article entitled "Aluminum Chloride In The Treatment Of Symptomatic Athlete's Foot", by Doctors Leyden and Kligman, Archives of Dermatology, Vol. 111, pps. 1004–1010, 1975; and
 (B) An article entitled "Bacteriology" by Doctors Kligman, Leyden, et al, Journal of Investigative Dermatology, Vol. 67; pps. 160–168, 1976.

In article (A) these doctors stated that interdigital lesions of the feet (athlete's foot) are invariably regarded as infections caused by ringworm fungi. The doctors also stated that as they see it, athlete's foot becomes an itching, malodorous, uncomfortable disorder when large numbers of ordinary, nonvirulent bacteria proliferate in the fungus infected interspace. Symptomatic athlete's foot, therefore, is a fungal-bacterial complex, a collaborative enterprise. They also stated on page 1009 that suppression of bacteria is an essential requirement in treating symptomatic athlete's foot. Further, that the ideal, perhaps, would be a single agent with very broad spectrum coverage against dermatophytes, Gram-positive and Gram-negative bacteria, and Candida. It was further stated that their preference, aluminum chloride, combines broad spectrum antimicrobial activity with chemical drying, a two-pronged attack, and that they viewed drying as the decisive element. At the end publication (A), the doctors stated that they did not find aluminum chloride to be superior to carbol-fuchsin solution. The difference, an important one in their opinion, lies in aesthetics. That statement was probably made because carbol-fuchsin is a purple stain.

In the second publication (B) these same doctors stated that they were reformulating the concept of interdigital athlete's foot as a simple ringworm infection, and that it is only when native diphtheroids grow extensively in a site previously colonized by ringworm fungi that the disturbing signs of the disorder appear. The doctors pointed out that simple scaling is the work of the fungi (dermatophytosis simplex) but that it is the luxurious growth of the diphtheroids that brings on the sogginess, maceration, itching and malodor that typifies the condition (dermatophytosis complex). The doctors further point out that since symptomatic athlete's foot is a product of collaboration between a ringworm fungus and the resident bacterial population, the disease can be controlled, though not cured, by repressing the bacteria.

Regarding the instant invention, it is an important object of this invention to provide a treatment for athlete's foot that is economical, and may be sold over the counter rather than require a prescription. Applicant has discovered that vanillin is antimicrobial; that is, vanillin possesses antifungal and antibacterial activity. That antimicrobial activity covers the spectrum of Gram-positive and Gram-negative bacteria, yeast, and mold, to the special regard to Trichophyton interdigitale and Trichophyton rubrum, the "athlete's foot" molds. Vanillin may be formulized with other well known chemicals to provide a treatment in the form of a cream, gel, powder, liquid, aerosol liquid, aerosol powder, ointments, and the like. The vanillin may also be utilized in powder form in a controlled release dispenser for foot treatment of a shoe or other article of footwear overnight.

Applicant has discovered not only that vanillin has a high antimicrobial activity, but that vanillin in a solid state will sublime, and applicant has also invented a method of treating a shoe or other article of footwear by utilizing vanillin in a powder form packaged in a controlled release dispenser and placing the dispenser in the toe portion of a shoe or the like, leaving it there overnight. In the morning it may be removed and the user can wear the shoe during the day, relying on the condensed sublimate remaining in the shoe for treatment of athlete's foot.

DETAILED DESCRIPTION

Applicant has discovered that vanillin (3-methoxy-4-hydroxybenzaldehyde; 4-hydroxy-3-methoxybenzaldehyde) possesses antifungal and antibacterial activity to a very high extent. The same is true of ethyl vanillin (3-ethoxy-4-hydroxybenzaldehyde). This antimicrobial activity has a very broad spectrum coverage against dermatophytes, Candida, other yeast fungi, and mold fungi including Trichophyton interdigitale and Trichophyton rubrum, the athlete's foot molds, as well as Gram-positive and Gram-negative bacteria.

Experts have said that in addition to the fungi which initially cause athlete's foot, bacterial infections also can cause erythrasma, pyoderma, pseudomonas intertrigo, as well as various other moist, itching forms of dermatitis with peeling skin, splits between the toes and the other common signs of athlete's foot. The antimicrobial activity of vanillin is effective against these disorders as well as the strictly athlete's foot disorder.

Applicant has also ascertained that the concentrations of vanillin that are effective in laboratory antimicrobial tests range from a low of 2.5% to as high as 100%. However, a good working range lies between 2.5% through 20%, although this range is not critical. "Athlete's foot" can be defined as "a persistent, symptomatic skin disease of the foot caused by many factors including bacteria and fungi". It is known that corynebacteria species and pseudomonas species are common bacterial pathogens, in disorders of this nature.

From the foregoing, it appears that vanillin will be utilized in the treatment of a number of dermatitis afflictions which involve fungi, bacteria, or both, because of the great antimicrobial affect of vanillin.

The following formulations are given by way of example only, and not by way of limitation of all the formulations in which vanillin may be utilized:

EXAMPLE 1

Cream or Ointment

| Ingredients | % |
|---|---|
| Water | 63.5 |
| Stearic acid | 20.0 |
| Glycerine | 10.0 |

-continued

| Ingredients | % |
| --- | --- |
| Vanillin | 2.5 |
| Isopropyl myristate | 1.5 |
| Polysorbate-80 | 1.5 |
| Cetyl alcohol | 1.0 |

EXAMPLE 2

Gel

| Ingredients | % |
| --- | --- |
| Water | 31.7 |
| Glycerine | 38.0 |
| Poloxamer 407 | 24.3 |
| Vanillin | 6.0 |

EXAMPLE 3

Powder

| Ingredients | % |
| --- | --- |
| Talc | 65.0 |
| Silica, hydrated | 25.0 |
| Aluminum chlorohydrate | 7.5 |
| Vanillin | 2.5 |

EXAMPLE 4

Liquid

| Ingredients | % |
| --- | --- |
| Ethanol SDA-40 | 72.5 |
| Water | 25.0 |
| Vanillin | 2.5 |

EXAMPLE 5

Liquid

| Ingredients | % |
| --- | --- |
| Water | 47.0 |
| Ethanol SDA-40 | 47.0 |
| Salicylic acid | 2.5 |
| Benzocaine | 1.0 |
| Vanillin | 2.5 |

EXAMPLE 6

Aerosol Liquid

| Ingredients | % |
| --- | --- |
| Ethanol | 47.0 |
| Propylene glycol | 1.0 |
| Benzocaine | 1.0 |
| Vanillin | 1.0 |
| Propellant 11/Propellant 12, 50/50 | 50.0 |

EXAMPLE 7

Aerosol Powder

| Ingredients | % |
| --- | --- |
| Talc | 4.0 |
| Ethanol | 1.9 |
| Benzocaine | 0.5 |
| Vanillin | 0.5 |
| Hexadecyl alcohol | 0.1 |
| Propellant 11 | 65.0 |
| Propellant 12 | 28.0 |

In the aerosol formulae, the propellants are "FREON" or an equivalent, which evaporate upon discharge from the aerosol container. Therefore, the vanillin increases to 2.5% or more of the ingredients actually applied to the skin.

All of the above formulations are for topical application. In Example 3—Powder, the vanillin being in solid form, will sublime and if used on the foot in an article of footwear for athlete's foot disease, will condense in the footwear to not only helpfully affect the disease, but would also lend deodorization and sanitization of the article of footwear as well.

Since vanillin is adaptable to many different vehicles, has a melting point of 80° to 83° C., and is soluble in water, alcohol, and numerous other chemicals where creams and the like, gels, and liquids are desired, and may be utilized in powder form as exemplified in Example 3, the mixing of the ingredients which recite commonly known chemicals, would be apparent to any chemist and any laboratory technician skilled in this art. The ingredients may be combined in each formula in the order in which they are listed. Consequently, it is not necessary herein to specifically outline the method of mixing these formulations. Merck's Index, Eighth Edition, tells all the necessary characteristics of vanillin, with the exception that vanillin is an antimicrobial.

Applicant has also invented a method of indirectly treating dermatitis in the general nature of athlete's foot. This method includes the use of a controlled release dispenser of the general type of a "HERCON Controlled Release Dispenser", HERCON being a registered trademark of Health-Chem Corporation of New York City. This type of dispenser is set forth in literature of Health-Chem Corporation, and particularly set forth in U.S. Letters Pat. No. 3,705,938 issued December 12, 1972, entitled "Activated Polymeric Materials and Process for Making Same". One satisfactory type of such dispenser embodies a porous reservoir made of polymeric material over at least one face of which another non-porous sheet of polymeric material is secured, the active properties of the reservoir sheet being such that its contents will migrate through and appear on the surface of the non-porous sheet that does not contact the reservoir sheet.

Applicant's method comprises placing a controlled release dispenser in at least the toe portion of a shoe, leaving it there overnight. In the morning, the dispenser is removed and packaged in a non-release container or wrapper, and the shoe is worn during the day with the wearer relying upon the residue or sublimate remaining in the shoe of an antimicrobial such as vanillin. During the night the shoe has been deodorized and sanitized and if the vanillin has been placed in the dispenser in a powdered form, there will be a sublimate remaining in the shoe to act on the foot during the day. Such a dispenser may be repeatedly utilized in that manner for quite a long period of time. That method of procedure would eliminate specific topical application of vanillin to the foot and permit the user to acquire benefit without any discomfort from wearing something inside the shoe, although there would be no harm if the dispenser were thin enough to wear the same in a shoe.

It should also be noted that a desired perfume might be utilized with any vanillin formulation, if desired, but vanillin emits a pleasant vanilla odor which in many instances would negate the need for any additional fragrance or perfume in the product.

The discovery that vanillin is a highly affective antimicrobial, along with its simplicity of use in either a formula for topical application or by way of a controlled release dispenser is a distinct advantage in the treatment of certain types of dermatitis by way of a simple and economical product that may be sold over the counter and does not require a prescription.

I claim:

1. The method of treating athlete's foot which comprises exposing the tinea pedis infected area of the skin to the antifungal and antibacterial action of vanillin.

2. The method of treating athlete's foot which comprises subliming vanillin into contact with the tinea pedis infected area of the skin.

3. The method of treating athlete's foot which comprises dispensing vanillin in footwear, subliming the vanillin in the footwear into contact with the tinea pedis infected area of the foot of a wearer of the footwear and subjecting the fungi and bacteria of the tinea pedis to the antifungal and antibacterial action of the vanillin sublimate.

4. The method of claim 1 including the step of applying the vanillin to the infected area in a topical preparation containing from about 2.5 to 20% vanillin in a carrier.

* * * * *